(12) United States Patent
Nakama

(10) Patent No.: US 7,227,126 B2
(45) Date of Patent: Jun. 5, 2007

(54) LIGHT DETECTION DEVICE

(75) Inventor: Kenichi Nakama, Tokyo (JP)

(73) Assignee: Nippon Sheet Glass Company, Limited, Tokyo (JP)

( * ) Notice: Subject to any disclaimer, the term of this patent is extended or adjusted under 35 U.S.C. 154(b) by 0 days.

(21) Appl. No.: 11/142,020

(22) Filed: Jun. 1, 2005

(65) Prior Publication Data

US 2005/0269494 A1 Dec. 8, 2005

(30) Foreign Application Priority Data

Jun. 4, 2004 (JP) ............................. 2004-167565

(51) Int. Cl.
*H01J 5/16* (2006.01)
*G01J 1/58* (2006.01)

(52) U.S. Cl. ...................... 250/234; 250/458.1; 356/73

(58) Field of Classification Search ................ 250/234, 250/574, 227.11, 458.1; 356/73, 246; 422/55; 436/46

See application file for complete search history.

(56) References Cited

U.S. PATENT DOCUMENTS 6,930,314 B2 * 8/2005 Jackson et al. .......... 250/458.1

FOREIGN PATENT DOCUMENTS

JP 2001-505654 4/2001
WO WO 98/07022 2/1998

* cited by examiner

*Primary Examiner*—Kevin Pyo
(74) *Attorney, Agent, or Firm*—Colin P. Cahoon; Carstens & Cahoon, LLP

(57) ABSTRACT

A microplate reader includes a light emitting portion for irradiating each of a plurality of test samples with excitation light, a light receiving portion for receiving return light from each of the test samples, an XY stage for moving the light emitting portion and the light receiving portion to traverse and scan the test samples, and a display portion for radiating visible light of a visible quantity in response to detection of fluorescence emitted from the test samples. An operator determines whether the measured test sample has emitted fluorescence based on illumination of the display portion.

18 Claims, 5 Drawing Sheets

LIGHT DETECTION DEVICE

CROSS-REFERENCE TO RELATED APPLICATIONS

This application is based upon and claims the benefit of priority from prior Japanese Patent Application No. 2004-167565, filed on Jun. 4, 2004, the entire contents of which are incorporated herein by reference.

BACKGROUND OF THE INVENTION

The present invention relates to a light detection device for indicating whether faint characteristic return light is emitted from a test sample irradiated with excitation light.

A typical light detection device irradiates a test sample with excitation light and detects characteristic return light (luminescence, fluorescence, reflected light, scattered light) included in the return light from the test sample to analyze the test sample.

In a light detection device such as a fluorescence microscope or a microplate reader, test samples are accommodated in a plurality of wells formed on a microplate. A conventional light detection device irradiates the entire microplate with excitation light having a specific wavelength to generate an image of the entire surface of the microplate with an imaging device such as a charge-coupled device (CCD) camera. The light detection device performs image processing on a picture image or image data of a plurality of light emitting points (characteristic return light) on the microplate to display an image.

Japanese National Phase Laid-Open Publication No. 2001-505654 describes a light detection device including an integrated cooled CCD camera, an image processing computer, and a display. The integrated cooled CCD camera is arranged at an observing position in a fluorescence microscope optical system to generate an image of the entire microplate. The image data of the entire microplate generated by the CCD camera is retrieved in the computer and shown on the display. This type of light detection device is designed for use in, for example, a large inspection room to perform measurement on a large quantity of microplates, which conform to predetermined standards.

An operator using such a light detection device is unable to determine whether or not light having a wavelength differing from that of the excitation light, that is, characteristic return light such as fluorescence, has been emitted from the test sample until the image data of the microplate is processed by the computer and displayed on the display. The conventional light detection device is thus complicated, large, expensive, and difficult to carry. Moreover, it is difficult for the operator to determine whether characteristic return light is emitted from each test sample on the microplate by looking at the test samples.

SUMMARY OF THE INVENTION

It is an object of the present invention to provide a light detection device which is compact, easy to carry, inexpensive, and capable of indicating detection of faint characteristic return light in a simple manner.

One aspect of the present invention is a light detection device for irradiating each of a plurality of test samples, each accommodated in one of a plurality of measurement areas, with excitation light, and detecting characteristic return light from each of the test samples. Each measurement area has a predetermined dimension. The light detection device includes a light emitting portion for irradiating each measurement area with the excitation light. A light receiving portion receives the characteristic return light. The light receiving portion is spaced from the light emitting portion by a predetermined distance that is less than the predetermined dimension. A scanner moves the light emitting portion and the light receiving portion in a range including the plurality of measurement areas to scan the measurement areas. A display portion emits visible light in response to detection of the characteristic return light from the measurement area which is being irradiated with the excitation light. The display portion is arranged close to the light emitting portion and the light receiving portion and on a side of the light emitting portion and the light receiving portion that is opposite from the measurement area.

Another aspect of the present invention is a portable light detection device for irradiating each of a plurality of test samples, each accommodated in one of a plurality of measurement areas, with excitation light, and detecting characteristic return light from each of the test samples. Each measurement area has a predetermined dimension. The portable light detection device includes an excitation light source, first and second light guide rods, a visible light source, and a scanner. The first light guide rod is optically coupled to the excitation light source. The first light guide rod has a first light reflection surface including a first light emitting portion from which the excitation light is emitted to one of the measurement areas and a light receiving portion to which the characteristic return light enters. The light receiving portion is spaced from the first light emitting portion by a predetermined distance that is less than the predetermined dimension. The second light guide rod is optically coupled to the visible light source. The second light guide rod emits visible light in response to detection of the characteristic return light from said one of the measurement areas which is being irradiated with the excitation light. The second light guide rod extends along the first light guide rod and has a second light reflection surface including a second light emitting portion from which the visible light is emitted. The scanner moves the first and second light guide rods to scan the measurement areas.

Other aspects and advantages of the present invention will become apparent from the following description, taken in conjunction with the accompanying drawings, illustrating by way of example the principles of the invention.

BRIEF DESCRIPTION OF THE DRAWINGS

The invention, together with objects and advantages thereof, may best be understood by reference to the following description of the presently preferred embodiments together with the accompanying drawings in which.

DETAILED DESCRIPTION OF THE PREFERRED EMBODIMENTS

A light detection device according to a first embodiment of the present invention will now be described.

Figure 1:
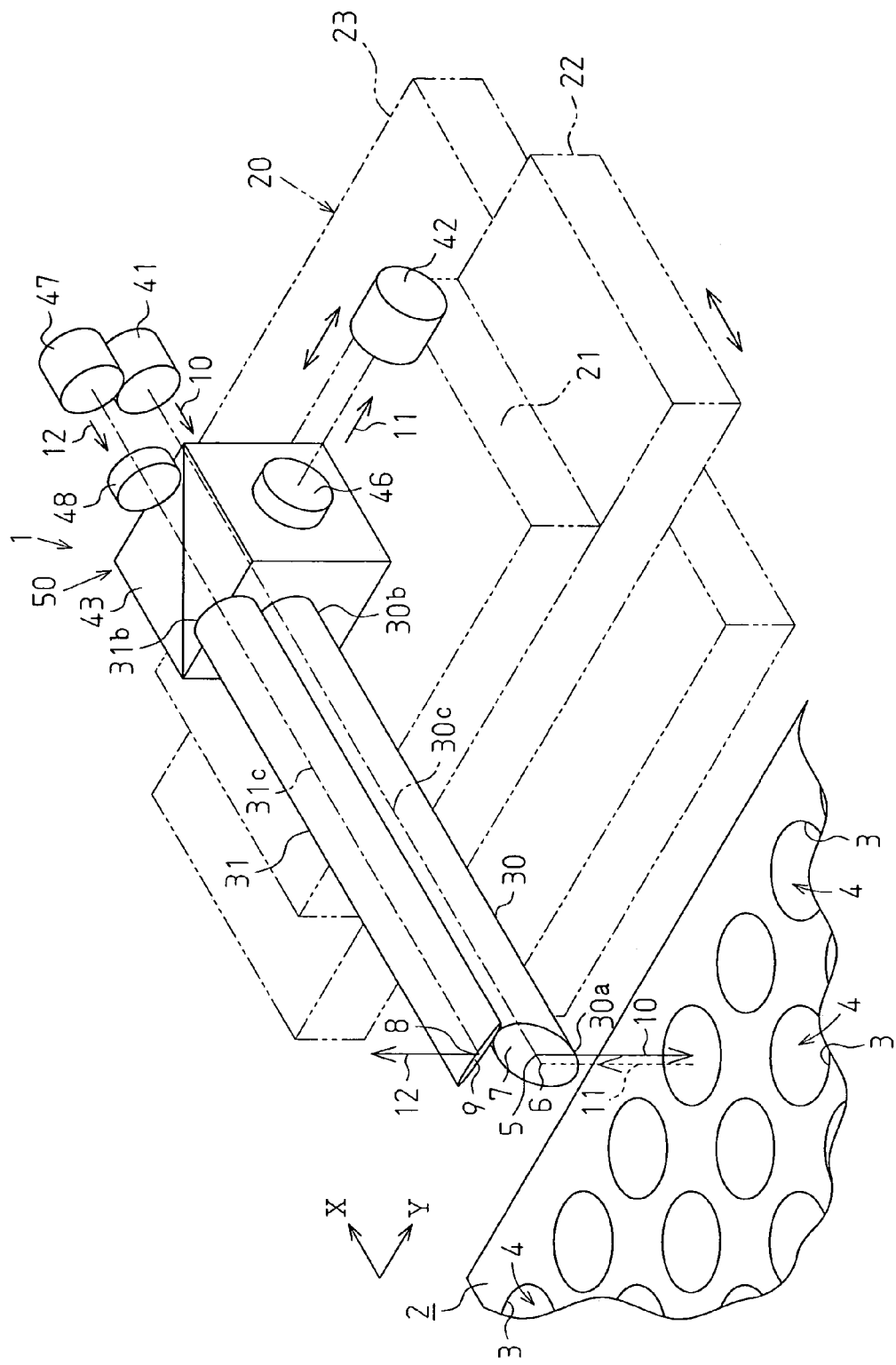
FIG. 1 is a perspective view showing a microplate reader according to a first embodiment of the present invention.

As shown in FIG. 1, a microplate reader 1, which functions as a light detection device, irradiates each of a plurality of test samples arranged on a microplate 2 with excitation light 10 to detect faint characteristic return light 11 from the test samples and indicate the result of such detection. The characteristic return light is light representing the characteristics of a test sample such as fluorescence, luminescence, reflected light, and scattered light included in the return light from a measurement area. The characteristic return light normally has a wavelength differing from that of the excitation light. In the following description, the characteristic return light 11 is fluorescence.

The microplate reader 1 qualitatively or quantitatively analyzes the test sample based on the wavelength and intensity of the characteristic return light 11.

A plurality of wells 3 are arranged two-dimensionally, that is, arranged so as to form a matrix, on a microplate 2, which functions as a substrate. Test samples 4 are each accommodated in one of the wells 3 on the microplate 2. Each well 3 defines the measurement area of its accommodating test sample 4. The upper surface of each test sample 4 defines the measurement area of the test sample 4.

Figure 2:
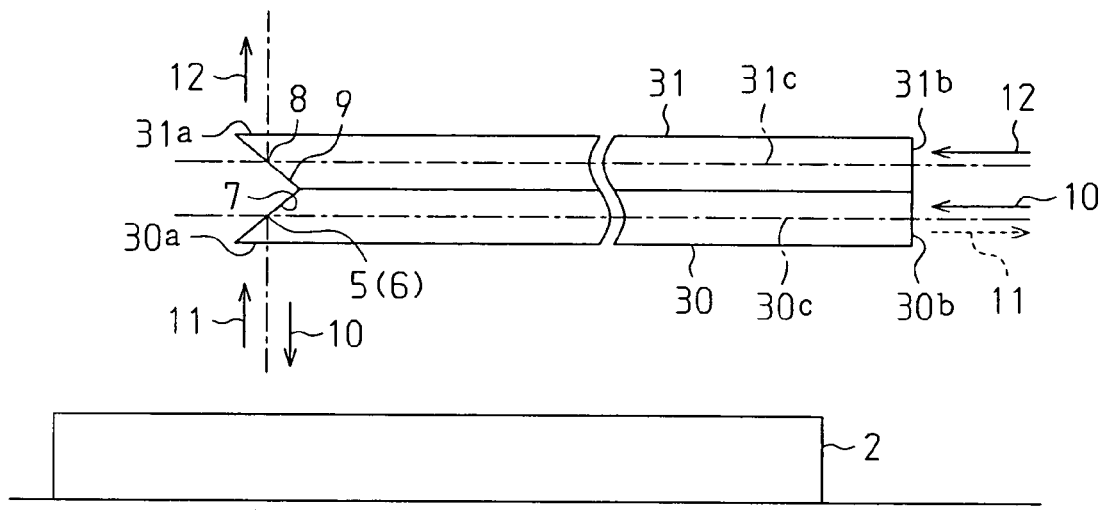
FIG. 2 is a side view showing glass light guide rods arranged above the microplate.

As shown in FIGS. 1 and 2, the microplate reader 1 includes a light emitting portion 5 and a light receiving portion 6. The light emitting portion 5 provides excitation light 10 to a test sample 4. The light receiving portion 6 receives fluorescence 11 from the test sample 4. The light emitting portion 5 and the light receiving portion 6 are arranged close to each other. More specifically, the distance between the light emitting portion 5 and the light receiving portion 6 is substantially equal to or less than the diameter of each well 3 (the dimension at the top surface of each test sample 4). The microplate reader 1 includes an XY stage 20 for moving the light emitting portion 5 and the light receiving portion 6 to sequentially scan the test samples 4.

The microplate reader 1 further includes a light emitting element 47 (visible light source) for emitting a visible light beam 12 and a display portion through which a visible light beam 12 with a visible quantity is emitted when fluorescence 11 is emitted from the test sample 4 that is irradiated with the excitation light 10. The display portion includes a reflecting portion 8 (a reflecting area or a light emitting point) for reflecting the visible light beam 12 toward the upward direction in FIG. 2. The visible light beam 12 emitted from the display portion notifies the operator that the test sample 4 undergoing measurement has emitted fluorescence 11. The reflecting portion 8 is arranged at a position close to the light emitting portion 5 and the light receiving portion 6 on the opposite side of the test samples 4.

The light emitting portion 5 and the light receiving portion 6 are formed as parts of a reflection surface 7. The reflection surface 7 is formed on a distal end 30a of a light guide rod 30 (first light guide rods). The light guide rod 30 is made of glass and formed by, for example, an optical fiber including a core and a cladding. As shown in FIG. 2, the reflection surface 7 is an inclined surface formed by polishing the distal end 30a of the light guide rod 30. The reflection surface 7 is inclined at an angle of 45 degrees with respect to the core axis 30c. The light emitting portion 5 and the light receiving portion 6 may be defined at the same position on the reflection surface 7 of the light guide rod 30.

The reflecting portion 8 is part of a reflection surface 9 formed on a distal end 31a of another light guide rod 31 (second light guide rod). The light guide rod 31 is made of glass and formed by, for example, an optical fiber including a core and a cladding. As shown in FIG. 2, the reflection surface 9 is an inclined surface formed by polishing the distal end 31a of the light guide rod 31. The reflection surface 9 is inclined at an angle of 45 degrees with respect to the core axis 31c. The light guide rod 31 is bonded to the light guide rod 30 with an adhesive such that the display portion emits the visible light beam 12 in the upward direction in FIG. 2, that is, such that the visible light beam 12 is emitted in the direction opposite to the direction in which the excitation light 10 is emitted (the downward direction in FIG. 2).

The two light guide rods 30 and 31 are optical fibers having the same structure and include the reflection surfaces 7 and 9 that are inclined at the same angle. The direction in which the display portion emits the visible light beam 12 is coaxial with the direction in which the light emitting portion 5 emits the excitation light 10.

In one embodiment, the light guide rods 31 and 30 may symmetrically arranged to each other so that the reflection surface 9 of the light guide rod 31 faces the reflection surface 7 of the light guide rod 30. In particular, the light guide rod 31 may extend parallel to the light guide rod 31, the light guide rod 30 may be positioned underneath the light guide rod 31, the reflection surfaces 7 and 9 may be flat, and the reflection surfaces 7 and 9 may form an angle of 90 degrees therebetween.

Figure 3:
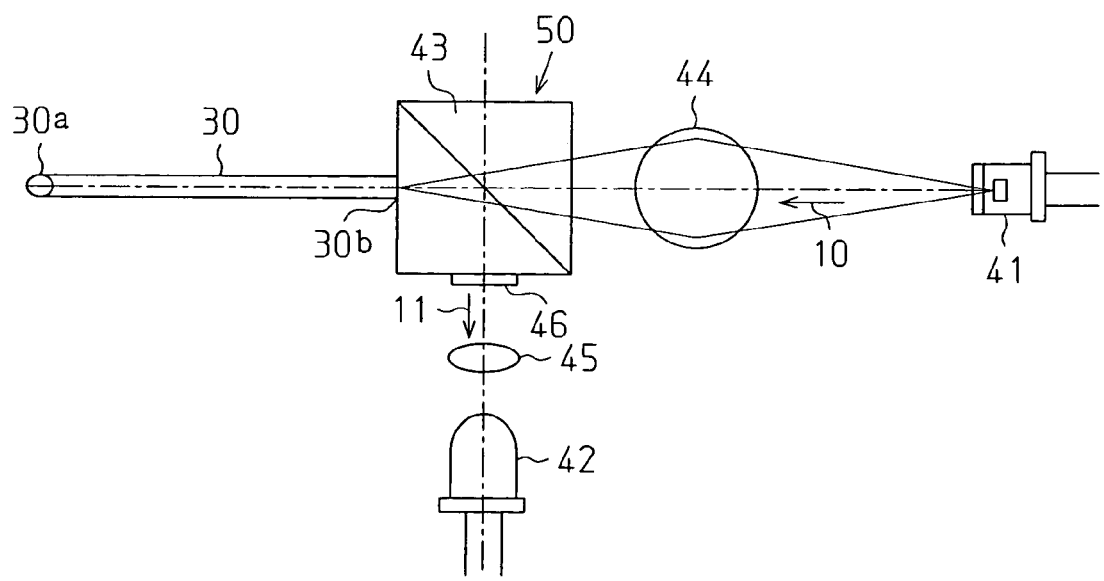
FIG. 3 is a plan view showing an optical system.

As shown in FIGS. 1 and 3, the microplate reader I includes a light source 41 for emitting the excitation light 10, a photodetector 42 for detecting the fluorescence 11, and an optical system 50 optically coupled to the light source 41 and the photodetector 42. The optical system 50 directs the excitation light 10 from the light source 41 to enter the basal end 30b of the light guide rod 30. The optical system 50 also directs the fluorescence 11 from the basal end 30b to enter the photodetector 42. In the first embodiment, the light source 41 is a laser light source such as a helium neon (HeNe) laser. The excitation light 10 is a laser light having a specific wavelength. The photodetector 42 is a photodiode.

As shown in FIG. 3, the optical system 50 includes a spherical lens 44, a wavelength division multiplexing element (beam splitter) 43 functioning as a wavelength division element, a converging lens 45, and a filter 46. The spherical lens 44 directs the excitation light 10 from the light source 41 to pass through the beam splitter 43 and converge at the basal end 30b of the light guide rod 30. The beam splitter 43 permits passage of the excitation light 10. Further, the beam splitter 43 selectively reflects only light having a wavelength differing from that of the excitation light 10 (i.e., the fluorescence 11) in the light returned via the basal end 30b of the light guide rod 30. The converging lens 45 focuses the reflected fluorescence 11 on the photodetector 42. The filter 46 cuts out the excitation light 10 to prevent the excitation light 10 from entering the photodetector 42. The spherical lens 44 and the converging lens 45 are not shown in FIG. 1.

The visible light source 47 generates a visible light beam 12 of a visible quantity and directs the visible light beam 12 to enter the basal end 31b of the light guide rod 31. The visible light source 47 is, for example, an LED. A wavelength selective filter 48 is arranged between the visible light source 47 and the basal end 31b of the light guide rod 31. The wavelength selective filter 48 permits passage of the visible light beam 12 from the visible light source 47 and blocks light having a wavelength other than that of the visible light beam 12. The filter 48 prevents light having a wavelength other than that of the visible light beam 12 (e.g., the fluorescence 11) from entering the visible light source 47.

Figure 4:
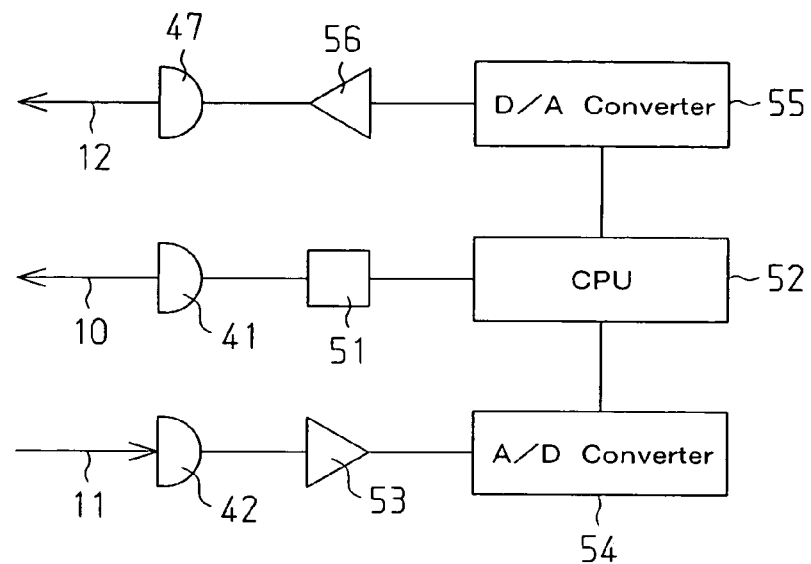
FIG. 4 is a block diagram of a control circuit for a light source and a photodetector of the microplate reader shown in FIG. 1.

A light emission control circuit for the light sources 41 and 47 will now be described. As shown in FIG. 4, the microplate reader 1 includes an oscillator 51, a CPU 52, an amplifier 53, and an A/D converter 54. The oscillator 51 is connected to the light source 41. The CPU 52 controls the oscillator 51 so that the light source 41 generates the excitation light 10. The amplifier 53 amplifies a detection signal from the photodetector 42. The A/D converter 54 converts the amplified detection signal (current signal) to a digital detection signal and provides the digital detection signal to the CPU 52.

The CPU 52 generates a digital control signal based on the digital detection signal. For example, when the value of the digital detection signal corresponding to the value of the detection signal from the photodetector 42 is greater than or equal to a threshold, the CPU 52 generates a digital control signal (ON signal) for activating the visible light source 47. When the value of the digital detection signal is less than the threshold, the CPU 52 generates a digital control signal (OFF signal) for inactivating the visible light source 47.

The microplate reader 1 further includes a D/A converter 55 and an amplifier 56. The D/A converter 55 converts the ON signal provided by the CPU 52 into a drive signal (analog voltage signal). The amplifier 56 amplifies the drive signal provided by the D/A converter 55 and provides the amplified drive signal to the visible light source 47. The visible light source 47 generates the visible light beam 12 in response to the amplified drive signal. Therefore, the CPU 52 functions as a control circuit for the visible light source 47.

As shown in FIG. 1, the beam splitter 43 is fixed on a movable table 21 of the XY stage 20. A holding member (not shown), which is fixed to the movable table 21, holds the components of the optical system 50 except for the beam splitter 43.

Figure 5:
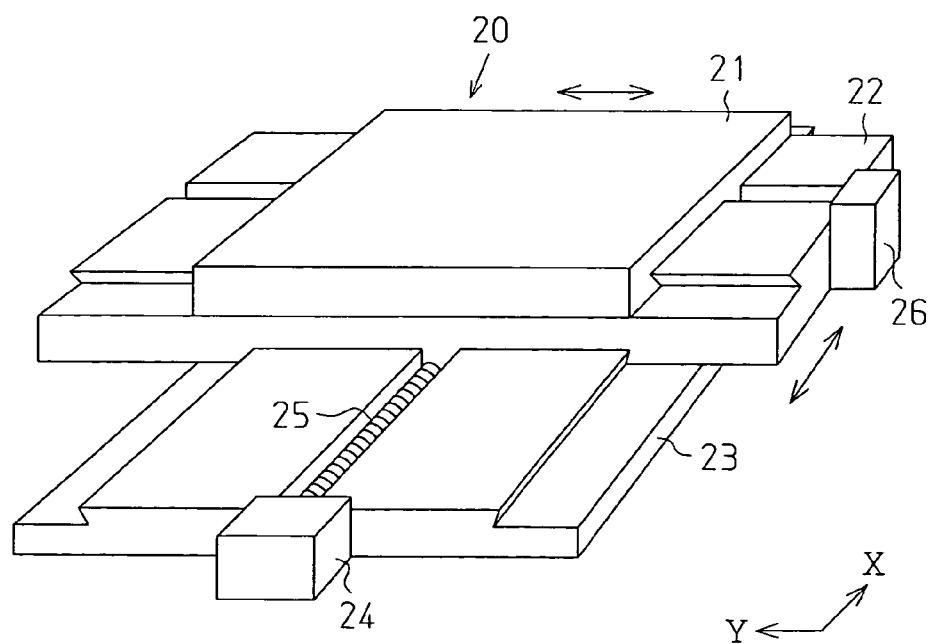
FIG. 5 is a perspective view showing an XY stage.

As shown FIG. 5, the XY stage 20 includes the movable table 21, a Y-drive table 22, and an X-drive table 23. The Y-drive table 22 supports the movable table 21 in a manner movable in the Y-axis direction. The X-drive table 23 supports the Y-drive table 22 in a manner movable in the X-axis direction. The X-drive table 23 includes an X-motor 24 and a screw shaft 25 extending in the X-axis direction. The X-motor 24 rotates its screw shaft 25 to move the Y-drive table 22 and the movable table 21 in the X-axis direction. The Y-drive table 22 includes a Y-motor 26 and a screw shaft (not shown) extending in the Y-axis direction. The Y-motor 26 rotates its screw shaft to move the movable table 21 in the Y-axis direction. The movement of the movable table 21 moves the light emitting portion 5 and the light receiving portion 6 along an XY plane.

Figure 6:
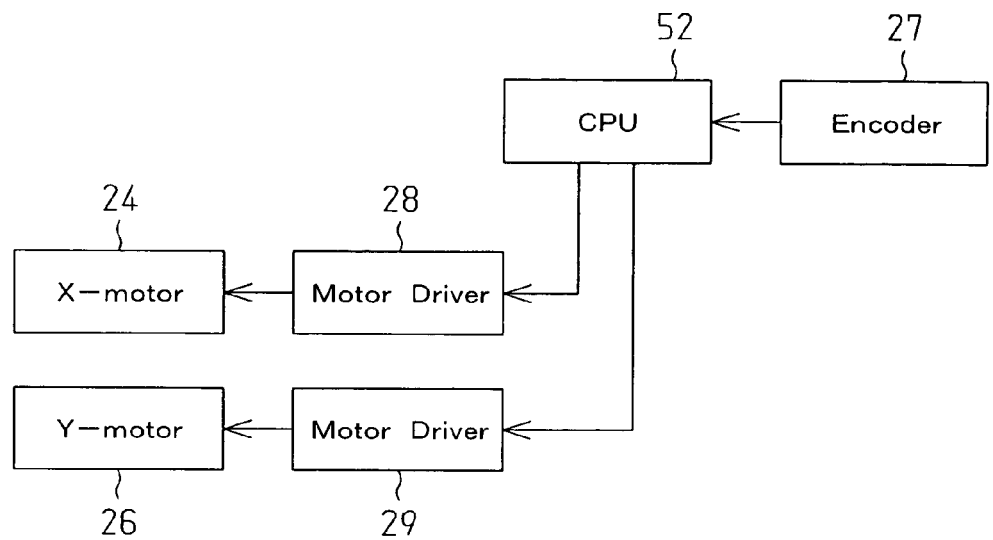
FIG. 6 is a block diagram showing the electrical configuration of the microplate reader.

Referring to FIG. 6, a scanner includes an encoder 27, an X-motor driver 28, a Y-motor driver 29, and the CPU 52. The encoder 27 detects the position (X and Y coordinates) of the movable table 21. The CPU 52 is connected to the encoder 27 and the motor drivers 28 and 29. The CPU 52 generates a motor control signal in accordance with a position signal indicating the position of the movable table 21, which is detected by the encoder 27, and provides the motor control signal to the motor drivers 28 and 29. The motor drivers 28 and 29 control the drive of the X-motor 24 and the Y-motor 26, respectively, in accordance with the motor control signal. For example, the CPU 52 drives the X-motor 24 and the Y-motor 26 so that the light emitting portion 5 and the light receiving portion 6 sequentially scan the matrix of the test samples 4 on the microplate 2 from the first column of the first row to the last column of the last row.

A pair of supporting members (not shown) fixed on the movable table 21 hold the basal end 30b of the light guide rod 30. The light guide rod 31 is fixed on top of the light guide rod 30.

Figure 7:
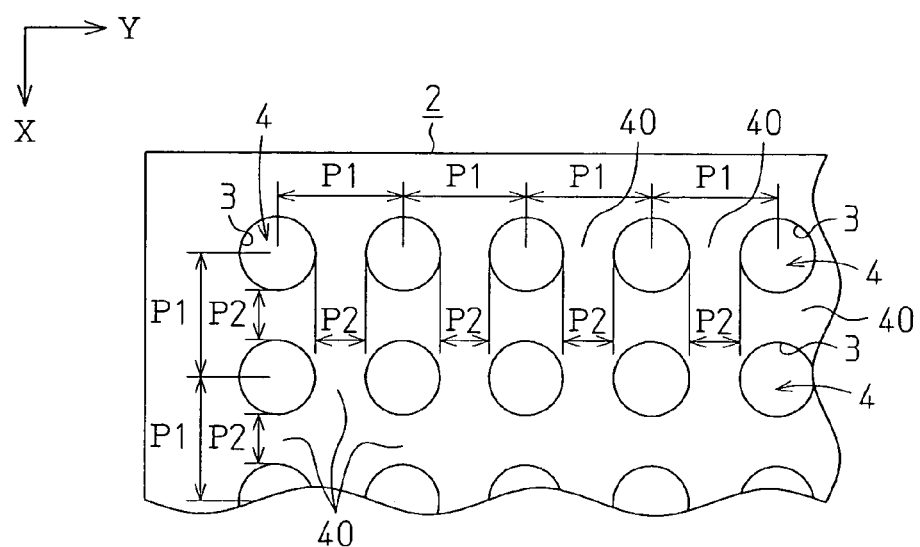
FIG. 7 is a partially enlarged plan view showing the microplate.

FIG. 7 is a partially enlarged view of the preferred microplate 2. The microplate 2 has a vacant region (region including no test sample 4) 40 defined between each pair of adjacent test samples 4. The vacant region 40 preferably has a dimension P2 that is at least 0.1 times the pitch P1 of the test samples 4 ($P2 \geq P1$). The dimension P2 of the vacant region 40 and the scanning speed of the scanner are determined so as to ensure that switching of the visible light source 47 from an activated state to an inactivated state (resetting) is completed within the period of time required for the scanner to move the light emitting portion 5 and the light receiving portion 6 across a vacant region 40 from a measured test sample 4 to the test sample 4 that is to be measured next.

The operation of the microplate reader 1 will now be described. The spherical lens 44 converges the excitation light 10 at the basal end 30b of the light guide rod 30. The excitation light 10 travels towards the distal end 30a of the light guide rod 30 and is reflected at the light emitting portion 5 on the reflection surface 7. The reflected excitation light 10 then travels in the downward direction perpendicular to the core axis 30c of the light guide rod 30 and enters one of the test samples 4 (see FIG. 1). Upon receiving the excitation light 10, the test sample 4 emits fluorescence 11. The fluorescence 11 is reflected at the light receiving portion 6 on the reflection surface 7 of the light guide rod 30 and sent into the light guide rod 30. The fluorescence 11 then travels towards the basal end 30b of the light guide rod 30 and is emitted from the basal end 30b. The fluorescence 11 is then reflected by the beam splitter 43 and passes through the filter 46. The fluorescence 11 is converged by the converging lens 45 and enters the photodetector 42. The photodetector 42 detects the intensity and/or the wavelength of the fluorescence 11 to generate a detection signal in accordance with the intensity and/or the wavelength. An arithmetic unit (not shown) performs qualitative and/or quantitative analysis on the test sample in accordance with the detection signal.

The detection signal of the photodetector 42 is amplified by the amplifier 53 and converted by the A/D converter 54 into a digital detection signal, which is provided to the CPU 52. The CPU 52 compares the value of the digital detection signal (output value of the photodetector 42) with a predetermined threshold. If the value is greater than or equal to the threshold, the CPU 52 provides an ON signal to the D/A converter 55. The D/A converter 55 converts the ON signal into an analog voltage signal. The analog voltage signal is amplified by the amplifier 56. The visible light source 47 generates the visible light beam 12 in response to the amplified analog voltage signal.

The visible light beam 12 passes through the filter 48 and is directed into the basal end 31b of the light guide rod 31. The visible light beam 12 travels along the light guide rod 31 and is reflected at a right angle by the reflecting portion 8 on the reflection surface 9 of the distal end 31a (see FIG. 1). The operator may thus determine whether or not the test sample 4 irradiated with the excitation light 10 has emitted fluorescence 11 by observing whether or not the reflecting portion 8 is illuminated.

If the value of the detection signal of the photodetector 42 is less than the threshold, the CPU 52 generates an OFF signal. In this case, the visible light source 47 does not generate a visible light beam 12 and the reflecting portion 8 is not illuminated. By observing that the reflecting portion 8 is not illuminated, the operator determines that the test sample 4 irradiated with the excitation light 10 has not emitted fluorescence 11.

The scanner mechanically moves the light guide rod 30. The light emitting portion 5 and the light receiving portion 6 scan the matrix of the test samples 4, which are arranged two-dimensionally on the microplate 2, sequentially from the test sample 4 in the first column of the first row to the test sample 4 in the last column of the last row. This results in generation of a detection signal that is in accordance with the intensity and/or the wavelength of the fluorescence 11 emitted from each of the test samples 4. Each detection signal is stored in association with the corresponding position of the movable table 21 and analyzed. Each test sample is analyzed qualitatively or quantitatively in accordance with the corresponding detection signal. The operator determines whether or not each of the test samples 4 has emitted fluorescence 11 based on whether or not the reflecting portion 8 is illuminated.

Relationship between Fluorescent Dye and Excitation Light

The test sample 4 is a biological sample such as DNA dyed with, for example, a fluorescent dye. To analyze the test sample 4 dyed with a fluorescent dye Cy3, a YAG laser device that oscillates the excitation light 10 having a wavelength of 532 nm may be used as the light source 41. In this case, return light from the test sample 4 includes the fluorescence 11, which has a wavelength of 570 nm.

To analyze a test sample 4 dyed with a fluorescent dye Cy5, a helium neon (HeNe) laser device that oscillates excitation light 10 having a wavelength of 633 nm may be used as the light source 41. In this case, return light from the test sample 4 includes the fluorescence 11 having a wavelength of 670 nm.

The first embodiment has the advantages described below.

(1) The microplate reader 1 includes the single light emitting portion 5 and the single light receiving portion 6, which are spaced from each other by a distance that is equal to or less than the dimension of the top surface of each test sample 4. The scanner moves the single light emitting portion 5 and the single light receiving portion 6 to sequentially scan the plurality of test samples 4. The light emitting portion 5 irradiates each test sample 4 with the excitation light 10. The light receiving portion 6 receives return light from each test sample 4. If the fluorescence 11 is included in the return light from each test sample 4, the reflecting portion 8 reflects the visible light beam 12 of a visible quantity to the opposite side of the light emitting portion 5 and the light receiving portion 6 from the test sample 4. By looking at the visible light beam 12, the operator easily recognizes that faint fluorescence 11 has been detected.

(2) One set of the light emitting portion 5 and the light receiving portion 6 is provided for the plurality of test samples 4. This structure eliminates the need for a large number of light guides as in the prior art example described above. Thus, the microplate reader 1 of the first embodiment is compact, portable and inexpensive.

(3) The light emitting portion 5 and the light receiving portion 6 are defined as parts of the reflection surface 7, which is formed on the distal end 30a of the glass light guide rod 30. This eliminates the need for additionally providing a light source or a photodetector on the distal end 30a of the light guide rod 30 and the need for arranging electric wiring on the light guide rod 30. The reflecting portion 8 is defined as part of the reflection surface 9 formed on the distal end 31a of the glass light guide rod 31. This eliminates the need for additionally providing a light source or a photodetector on the distal end 31a of the light guide rod 31 and the need for arranging electric wiring on the light guide rod 31. Thus, the microplate reader 1 of the first embodiment has high reliability and long durability.

(4) The light guide rods 30 and 31 are arranged so that the emission direction of the visible light beam 12 is opposite to the emission direction of the excitation light 10 (i.e., downward direction as viewed in FIG. 2). Therefore, the visible light beam 12 does not interfere with the fluorescence 11 and does not lower the accuracy of measurement of the fluorescence 11. Additionally, the light paths are deflected by the inclined reflection surfaces 7 and 9 formed on the distal ends 30a and 31a of the light guide rods 30 and 31. Therefore, the light detection device is relatively thin.

(5) The set of the light emitting portion 5 and the light receiving portion 6 scans the plurality of test samples 4. The light emitting portion 5 and the light receiving portion 6 are located at the same position on the distal end 30a of the single light guide rod 3. The light emitting portion 5 and the light receiving portion 6 are obtained by polishing the distal end 30a of the single light guide rod 30 to form the reflection surface 7. This eliminates the need for arranging more light guide rods 30 or changing the structure of the light guide rod 30 even when increasing the quantity of the test samples 4 that are to be analyzed. The same light guide rod 30 may be used regardless of the shape of the microplate 2 or the arrangement of the wells 3. Thus, the microplate reader 1 of the first embodiment is highly versatile and inexpensive.

(6) The excitation light 10 is guided from the light source 41 into the light guide rod 30 and sent from the light emitting portion 5 to each test sample 4. The fluorescence 11 from each test sample 4 is guided into the light guide rod 30 by the light receiving portion 6, travels through the light guide rod 30 in the direction opposite to the traveling direction of the excitation light 10, passes through the wavelength division multiplexing element 43 and the filter 46, and enters the photodetector 42. Loss in the excitation light 10 and the fluorescence 11 is small, and the detection accuracy of the fluorescence 11 from each test sample 4 is high.

(7) The visible light source 47 generates the visible light beam 12 of a visible quantity when one of the test samples 4, which is irradiated with the excitation light 10, emits the fluorescence 11. The visible light beam 12 is output from the reflecting portion 8 formed on the distal end 31a of the light guide rod 31. The operator may thus determine whether or not the test sample 4 has emitted the fluorescence 11 based on the visible light beam 12.

(8) The beam splitter 43 permits passage of the excitation light 10 from the light source 41. The beam splitter 43 also reflects light having a wavelength that differs from the wavelength of the excitation light 10 (i.e., fluorescence) in the light that returns via the basal end 30b of the light guide rod 30. The same optical system 50 may be used for the excitation light 10 and the fluorescence 11, which have different wavelengths. Accordingly, the microplate reader 1, which includes the simple optical system 50, is inexpensive.

(9) The scanner including the XY stage 20, the encoder 27, the CPU 60, and the motor drivers 28 and 29 scans the test samples 4 by mechanically moving the light emitting portion 5 and the light receiving portion 6 in a one-dimensional or two-dimensional manner with respect to the microplate 2, which is held in a fixed state. The scanner mechanically moves the single light emitting portion 5 and the single light receiving portion 6 in a two-dimensional manner to scan the plurality of test samples 4. This provides each of the test samples 4 with the excitation light 10 to detect the fluorescence 11 from each test sample 4. Accordingly, the microplate reader 1 is compact, portable, inexpensive, and highly versatile.

(10) The scanner mechanically moves the light emitting portion 5 and the light receiving portion 6, while the microplate 2 remains fixed. Therefore, the test samples 4 in the wells 3 are not subjected to any vibration or impact. This prevents a test sample 4 in one well 3 from moving to another well 3 and contaminating that test sample 4 of that well 3. Accordingly, the reliability of the measurement is high.

(11) The XY stage 20 of the scanner moves the movable table 21 in the X direction and in the Y direction along the XY plane that includes the test samples 4. The basal end 30b of the light guide rod 30 moves together with the movable table 21. Accordingly, the light guide rod 30 moves in the X direction and in the Y direction along the XY plane including the test samples 4. The XY stage 20 is thus capable of mechanically moving the single light emitting portion and the single light receiving portion in a two-dimensional manner to scan the plurality of test samples 4.

(12) The CPU 52 activates the visible light source 47 to generate the visible light beam 12 of a visible quantity when the value of the detection signal from the photodetector 42 is greater than or equal to the threshold. The visible light beam 12 thus generated brightly illuminates the reflecting portion 8. This notifies the operator that the fluorescence 11 has been detected.

(13) When using the microplate 2 that has vacant regions 40, the light emitting portion 5 and the light receiving portion 6 pass across a vacant region 40 when moving from one test sample 4 to another. During such movement, the value of the detection signal from the photodetector 42 becomes less than the predetermined threshold to assure that the CPU 52 inactivates the visible light source 47 before the light emitting portion 5 and the light receiving portion 6 reach the next the test sample 4. Therefore, the visible light source 47 is activated whenever detecting fluorescence 11 that renders the value of the detection signal from the photodetector 42 to be greater than or equal to the threshold. This improves the reliability of measurement. In other words, the fluorescence 11 emitted by a measured test sample 4 does not affect the measurement of the subsequent test sample 4.

(14) There is no need to attach the photodetector, the light source, and electric wiring to the glass light guide rods 30 and 31. Therefore, the light detection device is easily assembled and suitable for mass production.

Figure 8A:
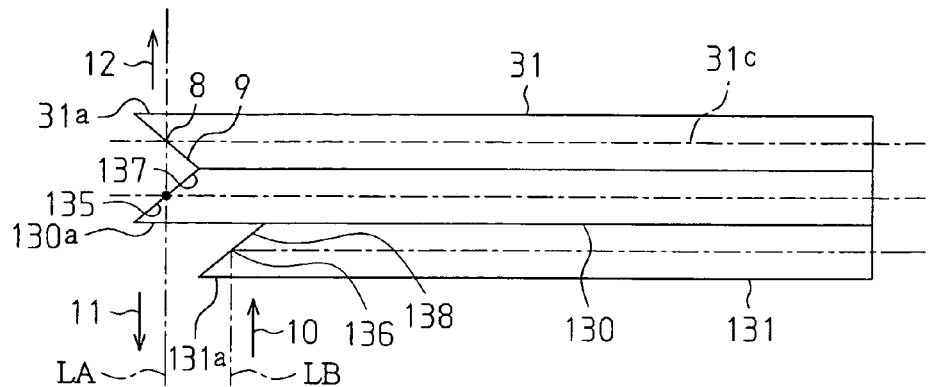
FIG. 8A is a side view showing light guide rods of a microplate reader according to a second embodiment of the present invention.
Figure 8B:
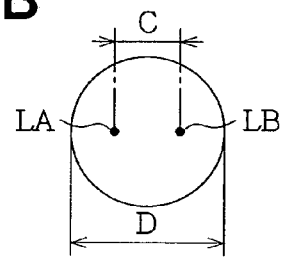
FIG. 8B is a diagram showing the distance between a light emitting portion and a light receiving portion and dimensions of a measurement area in FIG. 8A.

A microplate reader 1 according to a second embodiment of the present invention will now be described with reference to FIGS. 8A and 8B.

The microplate reader 1 of the second embodiment includes two glass light guide rods 130 and 131. The light guide rod 130 is used for excitation light, while the light guide rod 131 is used for return light. A light emitting portion 135 is defined by part of a reflection surface 137, which is formed on a distal end 130a of the light guide rod 130. A light receiving portion 136 is defined by part of a reflection surface 138, which is formed on a distal end 131a of the light guide rod 131.

The distance between the light emitting portion 135 and the light receiving portion 136 is equal to or less than the dimension of the top surface of each test sample 4. As shown in FIG. 8B, the distance C between a vertical line LA intersecting with the light emitting portion 135 and a vertical line LB intersecting with the light receiving portion 136 is less than the diameter D of the well 3, that is, the dimension of the top surface of each test sample 4. In the second embodiment, each of the light guide rods 130 and 131 is formed by an optical fiber including a core and a cladding. The light guide rods 130 and 131 are bonded to each other with an adhesive.

A reflecting portion 8 of a light guide rod 31 radiates a visible light beam 12 along the same axis as the excitation light 10 emitted from the light emitting portion 135 but in a direction opposite to the direction of the excitation light 10. In other respects, the second embodiment is the same as the first embodiment.

The second embodiment has the same advantages as the first embodiment.

A microplate reader 1A according to a third embodiment will now be described with reference to FIGS. 9A and 9B.

Figure 9A:
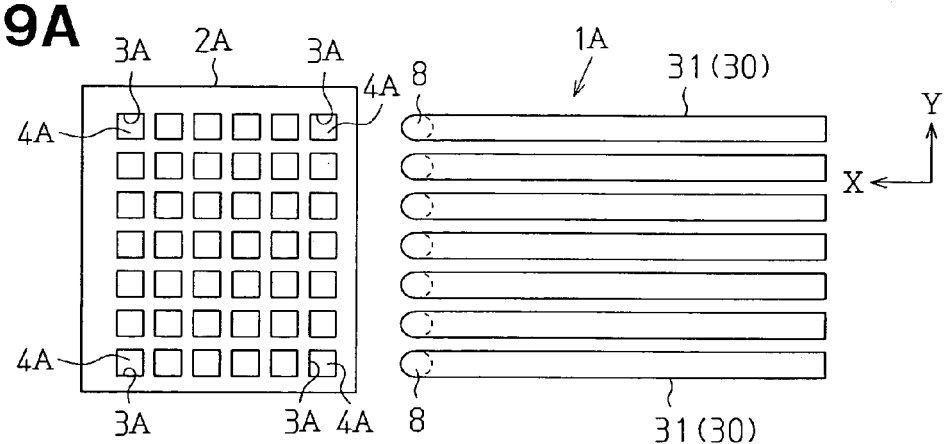
FIG. 9A is a partially enlarged view showing light guide rods of a microplate reader according to a third embodiment of the present invention.

As shown in FIG. 9A, a microplate 2A includes wells 3A which are arranged in a matrix of six columns and seven rows. A test sample 4A is accommodated in each of the wells 3A.

A light emitting portion 5 and a light receiving portion 6 are formed on a distal end 30a of each light guide rod 30. A reflecting portion 8 is formed on a distal end 31a of each light guide rod 31. The microplate reader 1A includes plural sets of light guide rods 30 and 31, with each set including one light guide rod 30 and one light guide rod 31. The number of sets of the light guide rods 30 and 31 is the same as the number of rows (seven rows) of the test samples 4A. In FIGS. 9A and 9B, the light guide rods 30 are hidden by the light guide rods 31.

Figure 9B:
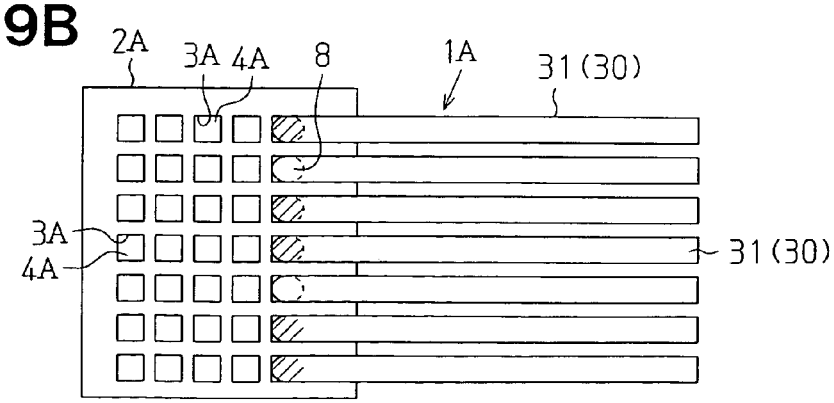
FIG. 9B is a partially enlarged view showing the light guide rods of the microplate reader during a measurement.

FIG. 9B shows a state in which the display portion of some of the light guide rods 31 (indicated by the oblique lines) are radiating a visible light beam 12.

In addition to the advantages (2), (5), (8) and (9) of the first embodiment, the third embodiment has the advantages described below.

(15) The number of the sets of the light guide rods 30 and 31 are the same as the number of the rows of the test samples 4A. The scanner, which has a plurality of light guide rods 30, completes the measurement of all the test samples 4A by moving the light emitting portions 5 and light receiving portions 6 of the light guide rods 30 only in the X direction to sequentially scan from the first column to the last column of the test samples on the microplate 2A. This enables elimination of the structure for moving the movable table 21 in the Y direction from the XY stage 20 shown in FIG. 5. Accordingly, the cost for manufacturing the microplate reader 1A is further reduced. Thus, the microplate reader 1A is inexpensive.

(16) Seven test samples 4A included in one column are measured simultaneously. This shortens the time required for measuring all the test samples 4A. Thus, the measurement efficiency of the microplate reader 1A is high.

It should be apparent to those skilled in the art that the present invention may be embodied in many other specific forms without departing from the spirit or scope of the invention. Particularly, it should be understood that the present invention may be embodied in the following forms.

The return light may be light other than fluorescence. For example, the return light may be luminescence, reflected light, or scattered light.

Instead of the glass light guide rod 30, an elongated vibration rod, of which the distal end is provided with a light source functioning like the light emitting portion and a photodetector functioning like the light receiving portion. In this case, the elongated rod includes electric wiring connected to the light source and the photodetector.

The light guide rod 30, 31, 130, or 131 need not necessarily be formed by an optical fiber including a core and a cladding. For example, the light guide rod may be a hollow light guide rod. This enlarges the usable wavelength range of the excitation light.

In the above embodiments, the light guide rods 30, 31, 130, and 131 need not necessarily be made of glass and may be made of resin. It is preferred that the resin be optically transparent for the excitation light and the return light.

In the above embodiments, the optical system 50, the electrical configuration shown in FIGS. 4 and 6 may be integrated into one module with the supporting member supporting the basal ends 30b and 31b of the light guide rods 30 and 31, and the module may be fixed to the movable table 21. The microplate reader 1 having this structure is easy to assemble and suitable for mass production.

In the first embodiment, a driver such as an electromagnet may be employed to vibrate the distal ends 30a and 31a of the light guide rods 30 and 31 in the Y-axis direction. In this case, the light emitting portion 5 and the light receiving portion 6 are vibrated when mechanically moved by the scanner in a two-dimensional manner to scan the plurality of test samples 4.

The present examples and embodiments are to be considered as illustrative and not restrictive, and the invention is not to be limited to the details given herein, but may be modified within the scope and equivalence of the appended claims.

What is claimed is:

1. A light detection device for irradiating each of a plurality of test samples, each accommodated in one of a plurality of measurement areas, with excitation light, and detecting characteristic return light from each of the test samples, wherein each measurement area has a predetermined dimension, the light detection device comprising:
   an excitation light emitting portion for irradiating each measurement area with the excitation light;
   a light receiving portion for receiving the characteristic return light, the light receiving portion being spaced from the excitation light emitting portion by a predetermined distance that is less than the predetermined dimension;
   a scanner for moving the excitation light emitting portion and the light receiving portion in a range including the plurality of measurement areas to scan the measurement areas; and
   a display portion for emitting visible light in response to detection of the characteristic return light from the measurement area which is being irradiated with the excitation light, wherein the display portion is arranged close to the excitation light emitting portion and the light receiving portion and on a side of the excitation light emitting portion and the light receiving portion that is opposite from the measurement area.

2. The light detection device according to claim 1, wherein the display portion is illuminated by the visible light.

3. The light detection device according to claim 2, further comprising:
   a light source for generating the excitation light;
   a photodetector for detecting the return light;
   an optical system optically coupled to the light source and the photodetector, the optical system directing the excitation light to enter a basal end of the first light guide rod and directing the return light, which has passed through the light receiving portion and the basal end of the first light guide rod, to enter the photodetector; and
   a visible light source for generating the visible light in a visible quantity and provides the visible light to a basal end of the second light guide rod.

4. The light detection device according to claim 3, wherein the optical system includes a wavelength division element for permitting passage of the excitation light and reflecting substantially only light having a wavelength differing from that of the excitation light in the return light.

5. The light detection device according to claim 4, wherein the visible light source and the optical system are arranged so that the visible light passes through part of the optical system before entering the basal end of the second light guide rod.

6. The light detection device according to claim 4, further comprising:
   a control circuit for causing the visible light source to generate the visible light in a visible quantity when the photodetector outputs a detection signal that is greater than or equal to a predetermined threshold.

7. The light detection device according to claim 1, further comprising:
   a first light guide rod made of glass and having a first reflection surface; and
   a second light guide rod made of glass and having a second reflection surface, wherein:
   the excitation light emitting portion and the light receiving portion are each defined by part of the reflection surface of the first light guide rod;
   the display portion is defined by part of the second reflection surface; and
   the first and second reflection surfaces are arranged so that the first and second light guide rods respectively emit the excitation light and the visible light in opposite directions.

8. The light detection device according to claim 7, wherein the excitation light emitting portion and the light receiving portion are located at the same position on the first reflection surface.

9. The light detection device according to claim 8, wherein:
   the plurality of measurement areas are arranged on a substrate in a matrix including a plurality of rows;
   the first light guide rod and the second light guide are integrated with each other to form a light guide rod set; and
   the light guide rod set being in a quantity that is the same as the number of the rows in the matrix.

10. The light detection device according to claim 7, wherein:
the plurality of measurement areas are arranged in a one-dimensional or two-dimensional manner on a substrate; and
the scanner holds the substrate in a fixed state and mechanically moves the excitation light emitting portion and the light receiving portion in a one-dimensional or two-dimensional manner to scan the plurality of measurement areas.

11. The light detection device according to claim 10, wherein the scanner includes an XY stage for moving the first light guide rod in a two-dimensional manner.

12. The light detection device according to claim 1, wherein:
a vacant region with a predetermined dimension is defined between an adjacent pair of the measurement areas; and
the dimension of the vacant region and the operating speed of the scanner are determined so that switching of the visible light source from an activated state to an inactivated state is completed within a period of time required for the scanner to move the excitation light emitting portion and the light receiving portion across the vacant region from one of the measurement areas to the next measurement area.

13. A portable light detection device for irradiating each of a plurality of test samples, each accommodated in one of a plurality of measurement areas, with excitation light, and detecting characteristic return light from each of the test samples, wherein each measurement area has a predetermined dimension, the light detection device comprising:
an excitation light source;
a first light guide rod optically coupled to the excitation light source, the first light guide rod having a first light reflection surface including a first light emitting portion from which the excitation light is emitted to one of the measurement areas and a light receiving portion to which the characteristic return light enters, wherein the light receiving portion is spaced from the first light emitting portion by a predetermined distance that is less than the predetermined dimension;
a visible light source;
a second light guide rod optically coupled to the visible light source for emitting visible light in response to detection of the characteristic return light from said one of the measurement areas which is being irradiated with the excitation light, the second light guide rod extending along the first light guide rod and having a second light reflection surface including a second light emitting portion from which the visible light is emitted; and
a scanner for moving the first and second light guide rods to scan the measurement areas.

14. The portable light detection device according to claim 13, wherein the first light guide rod extends parallel to the second light guide rod.

15. The portable light detection device according to claim 14, wherein the first and second light guide rods are optical fibers bonded to each other.

16. The portable light detection device according to claim 13, wherein the first light guide rod is positioned underneath the second light guide rod.

17. The portable light detection device according to claim 13, wherein the first reflection surface and the second reflection surface are flat and form an angle of 90 degrees therebetween.

18. The portable light detection device according to claim 13, wherein the second light emitting portion emits the visible light beam in the direction opposite to the direction in which the excitation light is emitted from the first light emitting portion.

* * * * *